United States Patent
Henshaw

(10) Patent No.: US 10,509,007 B1
(45) Date of Patent: Dec. 17, 2019

(54) MEASUREMENT OF GASES

(71) Applicant: Aeroqual Limited, Auckland (NZ)

(72) Inventor: Geoffrey Stephen Henshaw, Auckland (NZ)

(73) Assignee: Aeroqual Limited, Auckland (NZ)

( * ) Notice: Subject to any disclaimer, the term of this patent is extended or adjusted under 35 U.S.C. 154(b) by 742 days.

(21) Appl. No.: 14/973,934

(22) Filed: Dec. 18, 2015

Related U.S. Application Data

(60) Provisional application No. 62/093,455, filed on Dec. 18, 2014.

(51) Int. Cl.
*G01N 27/49* (2006.01)
*G01N 27/407* (2006.01)
*G01N 33/00* (2006.01)
*G01N 1/34* (2006.01)

(52) U.S. Cl.
CPC ............ *G01N 27/407* (2013.01); *G01N 1/34* (2013.01); *G01N 33/004* (2013.01); *G01N 33/0036* (2013.01); *G01N 33/0039* (2013.01); *G01N 33/0042* (2013.01); *G01N 33/0044* (2013.01)

(58) Field of Classification Search
CPC .......... G01N 27/4045; G01N 27/4074; G01N 27/404–407; G01N 27/409; G01N 27/419; G01N 27/41; G01N 33/497; A61B 5/08; A61B 5/097; A61B 5/082; A61M 16/085; A61M 2016/102; G01M 15/10; G01M 15/102; G01M 15/104
See application file for complete search history.

(56) References Cited

U.S. PATENT DOCUMENTS

| | | | | |
|---|---|---|---|---|
| 6,284,545 | B1 * | 9/2001 | Warburton | G01N 27/4045 422/50 |
| 8,597,580 | B2 * | 12/2013 | von Bahr | A61B 5/0803 422/84 |
| 2002/0090735 | A1 * | 7/2002 | Kishkovich | G01N 21/76 436/111 |
| 2011/0048108 | A1 * | 3/2011 | Yamagishi | G01N 33/0037 73/31.06 |

(Continued)

FOREIGN PATENT DOCUMENTS

GB 1249403 A 10/1971

OTHER PUBLICATIONS

Alexy et al.; "Disposable optochemical sensor chip for nitrogen dioxide detection based on oxidation of N,N'-diphenyl-1, 4-phenylenediamine"; Sensors and Actuators b: Chemical: International Journal Devoted to Research and Development of Physical and Chemical Transducers, Elsevier S.A., Ch, vol. 114, No. 2, Apr. 26, 2006, pp. 916-927.

(Continued)

*Primary Examiner* — Gurpreet Kaur

(74) *Attorney, Agent, or Firm* — James Creighton Wray

(57) ABSTRACT

Interference signals from other gases in an air sample are eliminated by flowing an air sample directly to an electrochemical gas sensor and subsequently flowing an air sample through a selective scrubber and removing the target gas of interest before flowing the sample to the electrochemical gas sensor. The difference in responses of the electrochemical gas sensor is directly proportional to the concentration of the target gas of interest in the air sample.

14 Claims, 1 Drawing Sheet

(56) References Cited

U.S. PATENT DOCUMENTS

| | | | | |
|---|---|---|---|---|
| 2011/0077545 A1* | 3/2011 | Eichler | ............... | A61B 5/097 |
| | | | | 600/538 |
| 2013/0278427 A1 | 10/2013 | Setton | | |
| 2014/0174154 A1* | 6/2014 | Marra | ............... | G01N 1/2273 |
| | | | | 73/31.01 |
| 2017/0065208 A1* | 3/2017 | Furusaki | ............... | A61B 5/082 |

OTHER PUBLICATIONS

Kroon, D.J., "Analysis of ambient air", Journal of Physics E. Scientific Instrument, IOP Publishing, Bristol, GB, vol. 11, No. 6, Jun. 1, 1978, pp. 497-507.

Sauter et al.; "Development of Modular Ozone Sensor System for application in practical use", Sensors and Actuators b: Chemical: International Journal Devoted to Research and Development of Physical and Chemical Transducers, Elsevier S.A., Ch,, vol. 69, No. 1-2, Sep. 10, 2000, pp. 1-9.

* cited by examiner

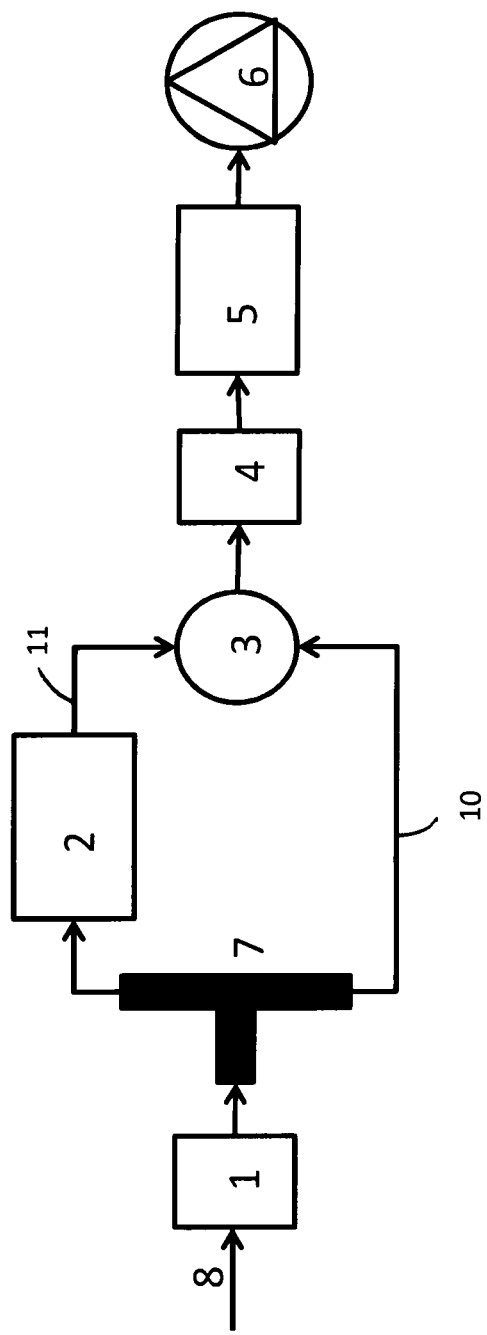

MEASUREMENT OF GASES

This application claims the benefit of U.S. Provisional Application No. 62/093,455 filed Dec. 18, 2014, which is hereby incorporated by reference in its entirety as if fully set forth herein.

BACKGROUND OF THE INVENTION

The measurement of low levels of gases in ambient air by electrochemical gas sensors is made difficult due to interferences such as humidity, temperature and other gases to which electrochemical sensors respond.

SUMMARY OF THE INVENTION

The invention solves the problem and compensates for those interferences by using a comparative measurement between two different states. The first state is one in which the sensor responds to a sample of air which includes the gas of interest plus the combination of interferences. The second state is one in which the gas of interest is removed from the sample using a selective scrubber, and the sensor responds to the combination of interferences. The concentration of the gas of interest in the incoming air sample is proportional to the difference between the electrochemical sensor signals in first and second states. This can be achieved with a new measurement system as described herein.

BRIEF DESCRIPTION OF THE DRAWINGS

FIG. 1 is a schematic representation of the apparatus, system and method of the invention.

DETAILED DESCRIPTION

FIG. 1 is a schematic representation of the apparatus, system and method of the invention. In FIG. 1, the numeral 1 represents an optional selective scrubber. Element 2 is a selective scrubber for the gas of interest to be determined. Element 3 represents a valve or a combination of valves that can be controlled to switch at a specific interval between the gas streams to the electrochemical sensor 5 in a housing. Element 4 represents a nafion tubing to buffer humidity. Pump 6 brings the air flow to the electrochemical sensor 5. T 7 allows the incoming air sample 8 to be routed through scrubber 2 or directly to the sensor. Valve 3 either directs the incoming air sample 8 or the sample which has been scrubbed by the target gas scrubber 2 through the humidity buffer 4 to the electrochemical sensor or directs the incoming air sample 8 through the humidity buffer 4 to electrochemical sensor 5, bypassing the scrubber. The concentration of the gas of interest in the incoming air sample is proportional to the difference between the electrochemical sensor signals in first and second states.

The electrochemical sensors 5 that may be deployed in the improved instrument include sensors for the measurement of $SO_2$, $H_2S$, CO, $NH_3$, $O_3$ and $NO_2$. Suitable selective scrubbers 2 depend on the gas of interest.

Example 1

Measurement of $SO_2$ was improved by using an electrochemical sensor 5 such as Alphasense $SO_2$-AF, a three-way solenoid valve 3 to switch sample flow between lines 10 and 11. Line 10 bypasses the selective target gas scrubber 2. Line 11 draws the incoming gas through scrubber 2. Scrubber 1 is a piece of PTFE tubing containing 0.2 g of silver wool. Scrubber 2 contains 10 g of marble (calcium and magnesium carbonate). The difference in response from the electrochemical sensor 5 when presented the air sample directly or via the scrubber 2 was found to be proportional to $SO_2$ concentration, and the measurement was substantively free of interference from temperature and humidity changes and carbon monoxide.

In other examples, a different scrubber 2 would be used to remove a different target gas and to eliminate its inclusion in gases sensed in sensor 5.

In other examples, plural scrubbers 2 are used with plural parallel lines 11. Switch 3 may have plural input connections for plural lines 11 to select individual lines 11, and the different individual lines 11 have different scrubbers 2 for connection to sensor 5.

In other examples, plural switches are connected between plural scrubbers and switch 3 to select specific scrubbers.

In one example, a device for determining the concentration of a target gas in ambient air transfers the sample air through an optional selective scrubber 1 to an electrochemical sensor 5. A solenoid valve 3 or valves cycles the air to the sensor 5 via a direct path 10 or a path 11 containing a selective scrubber 2. Electronics control the position of the valve 3 or valves and measure the sensor response at a sample interval between five and one thousand seconds after the valve 3 switches the sample flow.

The new method determines the concentration of a target gas in ambient air. The gas concentration is proportional to the difference in sensor signals between when the gas sample flows directly to the sensor 5 and when the gas sample flows via the selective scrubber 2 to the sensor.

The sensor signal after a predetermined time of sample flow through the scrubber 2 to the sensor 5 represents the signal of the sensor in the absence of the target gas. The sensor signal after a predetermined time of sample flow directly to the sensor represents the signal of the sensor in the presence of the target gas.

The sensor signal after a predetermined time of sample flow through the scrubber 2 to the sensor 5 represents the signal of the sensor in the absence of the target gas. The sensor signal after a predetermined time of sample flow directly to the sensor represents the signal of the sensor in the presence of the target gas.

In other examples, the electrochemical sensor is for the measurement of $SO_2$, $H_2S$, CO, $NH_3$, $O_3$ or $NO_2$.

For the measurement of $SO_2$, the first optional scrubber 1 is a catalyst containing a silver catalyst, $MnO_2$ catalyst, potassium iodide or ferrous sulphate for the scrubbing of ozone and $NO_2$, and selective scrubber 2 contains activated carbon, marble chips, calcium carbonate or an adsorbent for acidic gases.

For the measurement of $H_2S$, the first optional scrubber 1 is a catalyst containing a silver catalyst, $MnO_2$ catalyst or potassium iodide for the scrubbing of ozone and $NO_2$, and selective scrubber 2 contains activated carbon or iron oxides or a purafil chemisorbent for $H_2S$.

The invention provides a device for determining the concentration of a target gas in ambient air 8 which transfers the sample air through an optional selective scrubber 1 to an electrochemical sensor 5, via a solenoid valve 3 or valves which cycles the air to the sensor via a direct path or a path containing a selective scrubber 2. Electronics control the position of the valve 3 or valves and measure the sensor 5 response at a sample interval between 5 and 1000 seconds after the valve 3 switches the sample flow.

The invention provides a method of determining the concentration of a target gas in ambient air and where the gas concentration is proportional to the difference in sensor signals between when the gas sample flows directly to the sensor or flows via the selective scrubber 2.

In the new method the sensor signal after a predetermined time of sample flow through the scrubber 2 to the sensor 5 represents the signal of the sensor in the absence of the target gas. The sensor signal after a predetermined time of sample flow directly to the sensor 5 represents the signal of the sensor in the presence of the target gas.

In the new method the sensor signal after a predetermined time of sample flow through the scrubber 2 to the sensor 5 represents the signal of the sensor in the presence of the target gas, and the sensor signal after a predetermined time of sample flow directly to the sensor 5 represents the signal of the sensor in the absence of the target gas.

The invention provides a new device with the electrochemical sensor 5 for the measurement of $SO_2$, $H_2S$, CO, $NH_3$, $O_3$ or $NO_2$.

In a new device as described herein for the measurement of $SO_2$, the selective scrubber 1 includes a catalyst containing a silver catalyst, a $MnO_2$ catalyst, potassium iodide or ferrous sulphate for the scrubbing of ozone and $NO_2$, and selective scrubber 2 contains activated carbon, marble chips, calcium carbonate or an adsorbent for acidic gases.

In a new device described herein for the measurement of $H_2S$, the selective scrubber 1 includes a catalyst containing a silver catalyst, a $MnO_2$ catalyst, potassium iodide or ferrous sulphate for the scrubbing of ozone and $NO_2$, and selective scrubber 2 contains activated carbon, iron oxides or a purafil chemisorbent for $H_2S$.

While the invention has been described with reference to specific embodiments, modifications and variations of the invention may be constructed without departing from the scope of the invention, which is defined in the following claims.

I claim:

1. Apparatus comprising:
    an instrument adapted for measurement of one or more target gases in a sample of ambient air, further comprising:
    an input for the sample of ambient air,
    a first path having a first inlet and a first outlet,
    at least one additional second path having a second inlet and a second outlet,
    at least one multiple-way valve having a first input port connected to the first outlet, having a second input port connected to the second outlet and having an output port,
    a connection connected to the output port,
    a electrochemical gas sensor connected to the connection for receiving the sample of ambient air,
    a humidity buffer directly connected between the output port of the multiple-way valve and the electrochemical gas sensor,
    a flow inducer connected to the instrument for flowing the one or more target gases with the sample of ambient air in the first and the second paths through the multiple-way valve, the connection and the electrochemical gas sensor,
    a selective gas scrubber in the second path for removing a target gas from the sample of ambient air,
    a gas flow divider configured as a T having an inlet gas flow port at a bottom of the T and an outlet gas flow port at a top of the T for selectively supplying the sample of ambient air to the first input port or the second input port, and
    wherein the bottom of the T is connected to the input for the sample of ambient air and wherein one end of the top of the T is connected to the first inlet and another opposite end of the top of the T is connected to the second inlet.

2. The apparatus of claim 1, further comprising an input gas scrubber connected to the inlet port of the gas flow divider for removing selected gases from the sample of ambient air.

3. The apparatus of claim 2, wherein the selected gases removed by the input gas scrubber are $O_3$ and $NO_2$.

4. The apparatus of claim 1, wherein the flow inducer is a pump connected to the electrochemical gas sensor for drawing the sample of ambient air through the electrochemical gas sensor from the multiple-way valve and through the first or second path as determined by a condition of the multiple-way valve.

5. The apparatus of claim 4, wherein the multiple-way valve is a three-way valve.

6. The apparatus of claim 1, wherein the selective gas scrubber is selected to remove $SO_2$ or $H_2S$ from the sample of ambient air.

7. The apparatus of claim 1, comprising a method of determining the concentration of a target gas in ambient air comprising a device, wherein target gas concentration is proportional to a difference in sensor signals between when the sample of ambient air flows directly to the electrochemical gas sensor or flows to the electrochemical gas sensor via the selective scrubber of the target gas.

8. The apparatus of claim 1, wherein the electrochemical sensor is for the measurement of $SO_2$, $H_2S$, CO, $NH_3$, $O_3$ or $NO_2$.

9. The apparatus of claim 1, wherein the instrument is for the measurement of $SO_2$, wherein the selective scrubber contains activated carbon, marble chips, calcium carbonate or an adsorbent for acidic gases.

10. The apparatus of claim 1, further comprising a second selective scrubber connected to inlets of the paths.

11. The apparatus of claim 10, wherein the second selective scrubber comprises a catalyst containing a silver catalyst or $MnO_2$ catalyst or potassium iodide or ferrous sulphate for the scrubbing of ozone and $NO_2$.

12. The apparatus of claim 10, wherein the instrument is for the measurement of $H_2S$, wherein the second selective scrubber comprises a catalyst containing a silver catalyst, $MnO_2$ catalyst, potassium iodide or ferrous sulphate for the scrubbing of ozone and $NO_2$ and the selective scrubber of the target gas comprises activated carbon, iron oxides or a purafil chemisorbent for $H_2S$.

13. The apparatus of claim 1, wherein the instrument is for the measurement of ozone, wherein the selective scrubber comprises a catalyst containing a silver catalyst, $MnO_2$ catalyst or potassium iodide for the scrubbing of ozone.

14. The apparatus of claim 10, wherein the instrument is for the measurement of $NO_2$, wherein the second selective scrubber comprises a catalyst containing iron or silver or $MnO_2$ or potassium iodide for the scrubbing of ozone and the selective scrubber of the target gas comprises activated carbon, ferrous sulphate or a purafil chemisorbent for $NO_2$.

* * * * *